United States Patent
Ürögdi et al.

(10) Patent No.: US 6,180,787 B1
(45) Date of Patent: Jan. 30, 2001

(54) PROCESS FOR PREPARING O-(3-AMINO-2-HYDROXY-PROPYL)-HYDROXYMIC ACID HALIDES

(75) Inventors: László Ürögdi; Mihály Barabás; Ede Márványos, all of Budapest; Magdolna Török, Mátészalka; Zita Csákai, Kunszentmiklós, all of (HU)

(73) Assignee: Biorex Kutato es Fejleszto Rt., Veszprem-Szabadsagpuszta (HU)

( * ) Notice: Under 35 U.S.C. 154(b), the term of this patent shall be extended for 0 days.

(21) Appl. No.: 09/402,267

(22) PCT Filed: Dec. 5, 1997

(86) PCT No.: PCT/HU97/00082

§ 371 Date: Dec. 15, 1999

§ 102(e) Date: Dec. 15, 1999

(87) PCT Pub. No.: WO98/43948

PCT Pub. Date: Oct. 8, 1998

(30) Foreign Application Priority Data

Apr. 3, 1997 (HU) .................................................. 9700699

(51) Int. Cl.[7] ..................... C07D 295/125; C07C 239/20
(52) U.S. Cl. .......................... 544/124; 544/360; 546/193; 546/212; 546/232; 546/338; 564/256
(58) Field of Search ........................... 544/124; 564/256; 546/232

(56) References Cited

FOREIGN PATENT DOCUMENTS

90/08131 * 7/1990 (WO) .

* cited by examiner

Primary Examiner—Robert W. Ramsuer
(74) Attorney, Agent, or Firm—Finnegan, Henderson, Farabow, Garrett & Dunner, L.L.P.

(57) ABSTRACT

The present invention relates to a novel process for preparing O-(3-amino-2-hydroxy-propyl)-hydroxymic acid halides of formula (I) by reacting a carboxamide oxime of formula (II) wherein $R^1$ is as specified above with reactive 3-amino-2-hydroxy-propane derivative diazotizing the O-substituted carboxamide oxime thus obtained with sodium nitrite in the presence of hydrogen halide, decomposing the diazonium salt and if desired, separating the optically active enantiomers and/or reacting the resulting base with an organic or mineral acid wherein the carboxamide oxime of formula (II) is reacted with a 3-hydroxy azetidinium salt of formula (III) wherein $R^2$ and $R^3$ are a defined above and $Y^-$ is a salt forming anion, in a lower alcoholic, preferably ethanolic medium optionally containing water and made alkaline with an alkali hydroxide, and before diazotizing the O-substituted carboxamide oxime intermediate obtained, the reaction mixture is neutralised and the organic solvent is removed. The process according to the invention provides the compounds of formula (I) with higher yield compared to the prior art processes.

2 Claims, 1 Drawing Sheet

PROCESS FOR PREPARING O-(3-AMINO-2-HYDROXY-PROPYL)-HYDROXYMIC ACID HALIDES

TECHNICAL FIELD

Figure 1:
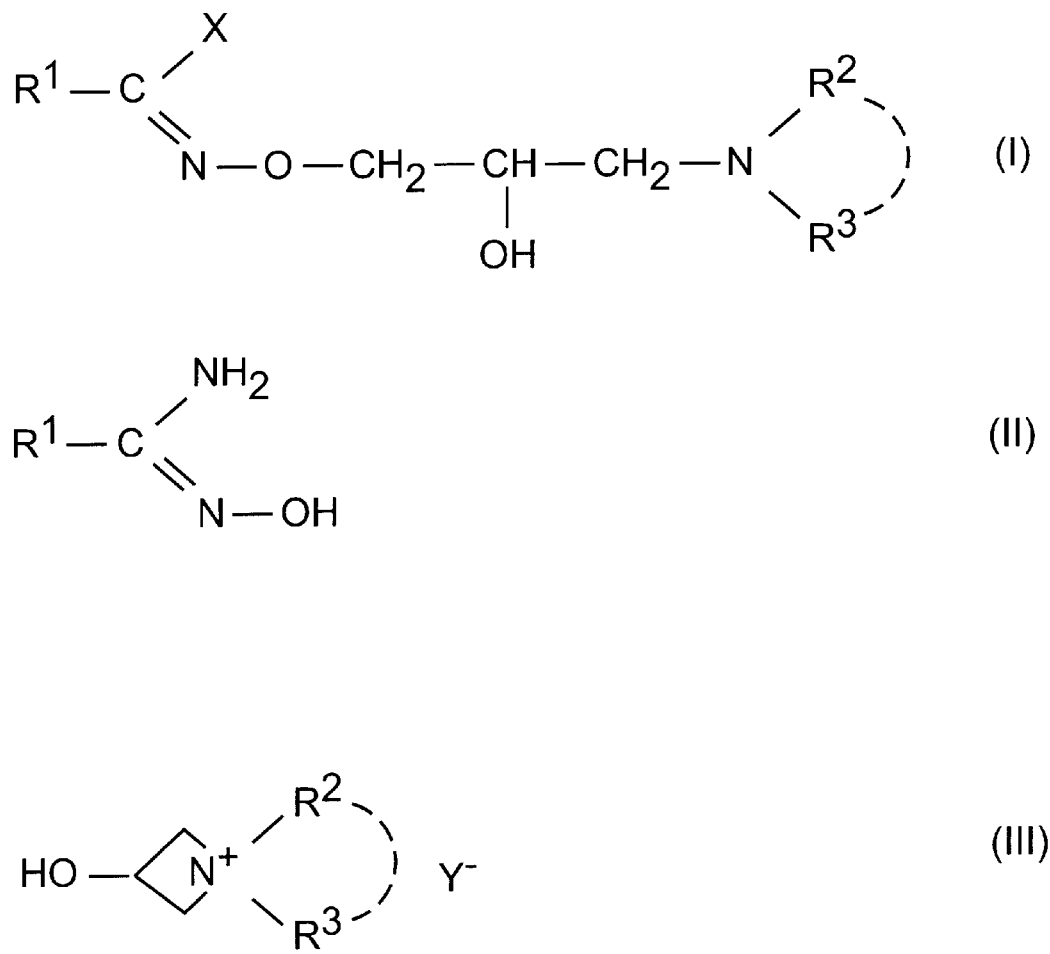

The present invention relates to a novel process for preparing O-(3-amino-2-hydroxy-propyl)-hydroxymic acid halides of the formula (I) wherein $R^1$ is phenyl, pyridyl or thienyl or substituted phenyl, wherein the one or more substituent(s) may be halo and/or haloalkyl and/or nitro, X is halo, $R^2$ and $R^3$ are independently from each other straight or branched lower alkyl or $R^2$ and $R^3$ together with the nitrogen connecting thereto form a saturated 5 to 7-membered heterocyclic group which may contain additional hetero atom and may be substituted.

The invention also relates to a process for preparing the acid addition salts and optically active forms of the above compounds.

BACKGROUND ART

O-(3-amino-2-hydroxy-propyl)-hydroxymic acid halides of the general formula (I) are well known as active substances in the treatment of pathological changes in the vascular system connected with diabetes mellitus, especially with diabetic angiopathy. These compounds are particularly described e.g. WO-A-90/04584.

O-(3-amino-2-hydroxy-propyl)-hydroxymic acid halides of the general formula (I) can be prepared in many different ways some of them being also described in the WO-A-90/04584.

Although the known synthesis routes for manufacture are suitable allow the preparation of the compounds of formula (I), they are not sufficient for the preparation of the said compounds in industrial scale. The disadvantage thereof is that they need reagents which are difficult to handle or prepare or comprise unfavourable reactions with non-satisfactory yields due to the possibility of side reactions. The urging need for the compounds of formula (I) requires a novel process which is secure, has a satisfactory yield and can be carried out under industrial conditions.

DISCLOSURE OF INVENTION

The present invention aims to provide a process for preparing O-(3-amino-2-hydroxy-propyl)-hydroxymic acid halides in industrial scale.

The present invention provides an industrially applicable process for preparing the compounds of the formula (I) by i) reacting an amidoxime compound of the formula (II) with a 3-hydroxy-azetidinium salt of the formula (III) wherein
$R^2$ and $R^3$ have the meaning as specified above and
$Y^-$ is a salt forming anion in a basic-alcoholic medium, ii) neutralizing the mixture and removing the organic solvent, iii) reacting the residue with sodium nitrite in aqueous medium in the presence of hydrochloric acid iv) decomposing the diazonium salt thus obtained and v) isolating the crude product of the formula (I) from the mixture.

Reactions of amidoxime compounds of the formula II and suitably substituted 3-amino-2-hydroxy-propane derivates (usually 1-halo- or 1,2-epoxy derivates) are described e.g. in GB Patent No. 1.582.029. However, the 3-hydroxy azetidinium salts of the formula (III) are more suitable reagents than the 1-halo- or 1,2-epoxi derivates used in the known reactions. Namely, compounds of the formula (III) are solid materials which can easily be prepared, isolated and stored unlike the reagents materials. The use thereof became known from WO-A-90/08131, but in the process described therein neither these nor the other two reagents are directly reacted with the compounds of the formula (II), but with an amidoxime complex prepared therefrom with alkali hydroxide or alkali and dimethyl formamide alcoholate or 1,3-dimethyl-2-imidazolidinone in a medium containing dimethyl formamide. Thus, O-substituted amidoxime derivatives were isolated which, however appear only as non-isolated intermediates in the reaction sequence according to the present invention.

Based on our observations efforts were made to eliminate the technologically difficult complex forming from the process and to avoid the use of dimethyl formamide as solvent. Dimethyl formamide is hazardous for health as it causes cancer, furthermore it is difficult to regenerate and purify and extremely difficult to make water-free. This is especially important as dimethyl formamide impurity must be minimized as pointed out in WO-A-90/08131. Moreover, it is preferable that the solvent contains only very small quantity of water, practically less than 1% to achieve a proper yield. An additional disadvantage of the use of dimethyl formamide is that it decomposes when exposed to light thus becoming contaminated by the toxic compounds envolved. It has been found that the reaction can safely and easily be carried out by redacting the compounds of the formulae (II) and (III) directly in a basic alcoholic medium which may also contain water. In respect of the outcome of the synthesis it is very useful that the O-substituted carboxamide oxime intermediate is not isolated from the reaction mixture, but directly reacted further after neutralizing the mixture and removing the organic solvent. It has also been found that the side products formed during the contracted steps can all be removed by one suitable isolation step and thus, the synthesis is appropriate for manufacturing the product in the desired purity.

Based on these observations, the invention provides a process for preparing compounds of the formula (I), wherein $R^1$ is phenyl, pyridyl or thienyl or substituted phenyl, wherein the one or more X is halo, $R^2$ and $R^3$ are independently from each other straight or branched lower alkyl or $R^2$ and $R^3$ together with the nitrogen connecting thereto form a 5 to 7-membered saturated heterocyclic group which may contain additional hetero atom and may be substituted, and the acid addition salts and optically active forms thereof by reacting a carboxamide oxime of the formula (II) wherein the meaning of $R^1$ is as specified above with a reactive 3-amino-2-hydroxy-propane derivate, diazotizing the resulting O-substituted carboxamide oxime with sodium nitrite in the presence of hydrohalide, decomposing the diazonium salt, isolating the product obtained and, if desired, separating the optically acive enantiomers and/or reacting the resulting base with an organic or mineral acid; which comprises reacting the carboxamide oxime of the formula (II) with a 3-hydroxy acetidinium salt of the formula (III) wherein $R^2$ and $R^3$ have the meaning as specified above and $Y^-$ is a salt forming anion in a $C_{1-4}$ alcoholic preferably ethanolic medium made alkaline with an alkali hydroxide, the said medium optionally containing water while neutralizing the reaction mixture and removing the organic solvent therefrom before diazotizing the resulting O-substituted carboxamide oxime intermediate.

BEST MODE FOR CARRYING OUT THE INVENTION

A preferred mode of carrying out the process according to the invention is as follows:

The carboxamid oxime of the formula (II) and the 3-hydroxy azetidinium salt of the formula (III) are reacted at stoichiometric ratio, however, it may be advantageous to apply the compound of the formula (III) in a slight excess. The reaction can be carried out with any order of addition of the reagents, preferably the compound of the formula (II) is added to the basic-alcoholic solution of the compound of the formula (III). As solvent preferably a $C_{1-4}$ alkanol, preferably ethanol is used and the reaction is carried out preferably with heating, most preferably at the boiling point of the solvent. After termination of the reaction, the mixture is cooled and neutralized with a mineral pressure. After removing the solvent the reaction mixture is diluted with water, the concentrated hydrochloric acid necessary for diazotizing is added, cooled to the diazotizing temperature and is diazotized by the addition of the sodium nitrite under cooling at a temperature of 0 to +5° C. The diazonium salt decomposes in situ into the corresponding hydroximoyl-halide derivative. To isolate the crude product, the reaction mixture is made alkaline with an inorganic alkali compound, extracted with an organic solvent non-miscible with water, preferably ethyl acetate, the extract is dried and concentrated, or directly an acid addition salt is formed from the product by adding a suitable acid to the mixture and separating the acid addition salt by filtration. The crude product can be purified by recrystallization or by any other way known in the art.

By using the above process, a properly pure product can be prepared with an economically satisfactory yield.

The advantage of the present invention lies in the fact that it makes possible to produce O-(3-amino-2-hydroxypropyl)-hydroxime acid halides by a safe and simple method also under industrial conditions.

The invention is further illustrated in the following examples:

EXAMPLE 1

N-[2-hydroxy-3-(1-piperidinyl)-propoxy]-3-pyrydine-carboximidoyl chloride (Z)-2-butenedioate 50.4 kg 2-hydroxy-4-azoniaspiro-[3,5]-nonane chloride was dissolved in and 28 l of water under stirring. To the solution 11.4 kg sodium hydroxide was added and the resulting milk-like mixture was stirred for an additional hour. While stirring, 420 l of ethanol and 35 kg 3-pyrydine-carboxamide oxime were added thereto and the mixture was heated under reflux for 1.5 hours followed by cooling the reaction mixture. 270–290 l of alcohol were distilled off and 110 l of deionized water and 45.5 l of concentrated hydrochloric acid were added followed by distilling off the remaining ethanol. To the oily residue 160 l of concentrated hydrochloric acid was added under cooling so that the temperature remained under 30° C. The solution was then cooled to 0° C. and for the diazotization a mixture of 17.7 kg sodium nitrite and 60 l of deionized water was added under permanent stirring and cooling while maintaining the temperature of the reaction mixture between 0 and +5° C. After the addition, the mixture was stirred for an additional hour at this temperature and for the decomposition of the nitrite excess 1.5 kg urea was added. After full decomposition of the nitrite (appr. 1.5 hours) to the reaction mixture 350 l ethyl acetate was added followed by alkalifying by the addition of 150–200 l concentrated sodium hydroxide under stirring and intensive cooling. The layers were separated, the organic phase washed with 2×70 l of water and dried over 15 kg anhydrous $Na_2SO_4$. The drying agent was filtered off, washed with 20 l ethyl acetate, the organic layers combined and the quantity of the N-[2-hydroxy-3-(piperidine-1-yl)-propoxy-3-pyrydine-carboximidoyl chloride base was determined. Maleic acid in calculated amount (21–22 kg) was added and the mixture was stirred for 4 hours. The product was separated in centrifuge, washed with 30 l acetone and the resulting crude product was dissolved in 70 l warm acetone and recrystallized. The product was separated in centrifuge and washed with 30 l acetone. After recrystallization, 50–55 kg N-[2-hydroxy-3-(1-piperidinyl)-propoxy]-3-piridine-carboximidoyl chloride (Z)-2-butenedioate (1:1) was obtained as pink beige crystals. (m.p. 123–124° C., acetone, yield: 53%).

IR (v, $KBr/cm^{-1}$): 3350, 2941, 1580, 1480, 1350, 1022, 982, 867, 702.

$^1$H-NMR (250 MHz, DMSO-$d_6$; ref.: DMSO-$d_6$=2.5δ (ppm): 9.00 (1H, s); 8.74 (1H, d); 8.18 (1H, d), 7.56(1H, dd); 6.03 (2H, s); 5.85–6.00 (1H, s/br); 4.21–4.37 (3H, m); 3.2–3.33 (2H, m); 2.49–2.55 (4H, m); 1.54–1.77 (6H, m). $^{13}$C-NMR (63 MHz, solvent: DMSO-$d_6$; ref.: DMSO-$d_6$=39.3.δ (ppm): 167.0 (COOH); 151.4, 127.9, 134.3, 123.5. 147.2 (pyrydine 2-3-4-5-6); 135.4 (CH=CH); 134.9 C/Cl/=NO); 77.2 (NOCH$_2$); 63.5 (CHOH, 58.3) (NCH$_2$); 52.9, 22.1, 21.2 (piperydine).

According to Example 1 the following compounds were prepared:

EXAMPLE 2

N-[2-hydroxy-3-(1-piperidinyl)-propoxy]-benzimidoyl chloride hydrochloride (m.p.: 140–144° C., isopropanol, yield: 66%) IR (KBr): 3234, 2951, 1504, 1448, 1389, 1289, 1119, 1059, 972, 768, 690.

EXAMPLE 3

N-{2-hydroxy-3-[-(4-methyl)-piperazinyl]-propoxy}-3-piridine-carboximidoyl chloride (Z)-2-butenedioate (1:2)

(m.p.: 174–175° C., ethanol, yield: 48%) IR (KBr): 3207, 1693, 1578, 1456, 1358, 1304, 1020, 974, 864, 702.

EXAMPLE 4

N-[2-hydroxy-3-(diethylamino)-propoxy]-3-piridine-carboximidoyl chloride hydrochloride (m.p.: 118–119° C., acetone, yield: 67%) IR (KBr): 3425, 3289, 2951, 2667, 1818, 1443, 1337, 1238, 1178, 1115, 1078, 1049, 997, 910, 804, 781, 696, 683 cm$^{-1}$

EXAMPLE 5

N-[2-hydroxy-3-(4-morpholinyl)-propoxy]-3-piridine-carboximidoyl chloride (Z)-2-butenedioate (m.p.: 137–138° C., isopropanol, yield: 52%) IR (KBr): 3310, 1580, 1483, 1464, 1443, 1354, 1072, 1024, 982

EXAMPLE 6

N-[2-hydroxy-3-(1-piperidinyl)-propoxy]-2-tiophene-carboximidoyl chloride hydrochloride (m.p.: 115–123° C., isopropanol-hexane, yield: 38%)

$^1$H-NMR (250 MHz, DMSO-$d_6$; ref.: DMSO-$d_6$=2.5δ (ppm): 10.2 (1H, s/br); 7.81, 7.63, 7.20 (1H, 1H, 1H, d, d, dd); 5.98 (1H, s/b); 4.42 (1H, s/b), 4.35 (2H, d); 3.60–2.90 (6H, m); 1.95–1.60 (4H, m); 1.45–1.20 (2H, m).

$^{13}$C-NMR (63 MHz DMSO-d$_6$; ref.: DMSO-d$_6$=39.3δ (ppm): 133.8 [C(Cl)=N]; 132.1, 130.3, 130.1. 127.6 (tiophene 3-2-5-4); 76.8 (NOCH$_2$); 63.2 (CHOH); 58.5 (CH$_2$N); 53.3, 51.8 (piperidine 2×NCH$_2$) 22.0, 21.9, 21.0 (piperidine 3×CH$_2$).

EXAMPLE 7

N-[2-hydroxy-3-(1-piperidinyl)-propoxy]-2-trifluoromethyl benzimidoyl chloride hydrochloride (m.p.: 119–123° C., ethylacetate, yield: 30%) IR (KBr): 3366, 2937, 2854; 2737, 2673, 2538, 1616, 1570, 1439, 1404, 1337, 1290, 1236, 1199, 1165, 1129, 1101, 1074, 1030, 984, 972, 933, 901, 829, 804, 788, 717, 699, 685, 646 cm$^{-1}$.

EXAMPLE 8

N-[2-hydroxy-3-(1-piperidinyl)-propoxy]-2'-nitrobenzimidoyl chloride hydrochloride (m.p.: 159–162° C., isopropanol, yield: 43%) IR (KBr): 3298, 2983, 2932, 2746, 1593, 1574, 1535, 1445, 1391, 1354, 1317, 1288 1242, 1198, 1117, 1092, 1069, 1020, 968, 947, 914, 852, 793, 756, 708, 577 cm$^{31}$.

EXAMPLE 9

(+) N-[2-hydroxy-3-(1-piperidine-1-yl)-propoxy]-3-piridine-carboximidoyl chloride (Z)-2-butenedioate (1:1)

2-hydroxy-4-azoniaspiro[3,5]nonane chloride and 3-piridine-carboxamide oxime were reacted according to Example 1 following the reaction steps up to separating the N-[2-hydroxy-3-(1-piperidine-1-yl)-propoxy]-3-piridine-carboximidoyl chloride with ethyl acetate. 15 g (50 mmole) N-[2-hydroxy-3-(1-piperidin-1-yl)-propoxy]-3-piridine-carboximidoyl-chloride in ethyl acetate was added dropwise to a mixed anhydride prepared from 13.52 g (50 mmole) N-(t-butoxycarbonyl)-L-phenylalanine and 5.0 ml ethyl chloroformate in dichlorometane by a method known per se and the mixture was stirred for an hour at room temperature. To isolate the ester thus obtained the solution was extracted with 2×200 ml aqueous acetic acid solution (10%) and 1×200 ml water, the organic layer was dried over anhydrous Na$_2$SO$_4$ and concentrated. The oily residue was dissolved in 140 ml acetone and to the solution 3.0 g maleic acid was added. Thus, 5.2 g (7.8 mmole, 16%) (−)N-[2-(N'-BOC-/L/-phenylalanyloxy)-3-(1-piperidinyl)-propoxy]-3-piridine-carboximidoyl chloride (Z)-2-butenedioate (1:1) salt (m.p.: 146.5–148° C.) was obtained.

5.2 g of the salt prepared as above was boiled in methanol for 1 hour. The solution was distilled to dryness and the residue was crystallized from 50 ml ethyl acetate giving 3.18 g (98%) (+) N-[2-hydroxy-3-(1-piperidin-1-yl)-propoxy]-3-piridine-carboximidoyl chloride (Z)-2-butenedioate (1:1) salt (m.p.: 136–137° C.). The IR and NMR spectrum of the compound corresponded to those of the racemic compound. According to chiral shift spectroscopy the compound was a homogenous enantiomer. The (−) isomer could be prepared in an analogous way, but using N-(t-butoxycarbonyl)/D/-phenylalanine as reagent.

The method according to the invention was compared with the method described in the prior art mentioned above. 3-piridine-carboxamide oxime was reacted with 3-piperidino-2-hydroxy-1-chloropropane prepared according to the method described in GB Patent 1.582.029 in absolute alcoholic medium. After termination of the reaction the solution was made alkaline, the product was extracted with benzene and from the base dihydrochloride was formed with gaseous hydrochloric acid. The O-(3-piperidino-2-hydroxy-1-propyl)-3-piridine-carboxamide oxime hydrochloride thus obtained was diazotized according to the method described in WO-A-90/04584, the diazonium salt was decomposed and the resulting product was reacted with maleic acid giving the product according to example 1. The final yield of the process based on the starting product was 38% while the same in Example 1 was 53%, which raised up to 60% during commercial production.

It can be established that the process according to the invention provides the compounds of the formula (I) with a higher yield compared to the prior art processes. A further advantage of the process according to the invention is the possibility to spare solvent. For preparing 1 kg product according to the process described in the present invention only 17 kg solvent was needed while the same according to the formerly known processes amounted to 40 kg. A further advantage of the process according to the invention in the industrial scale is that the technology time needed for the preparation of the compounds of the formula (I) is shorter. To produce 1 batch of the product related to 3 m$^3$ reactor volume according to the invention needed 4 consecutive shifts while the prior art processes needed 8 shifts.

Summarized, the process according to the present invention provides a method to prepare the O-(3-amino-2-hydroxy-propyl)-hydroximic acid halides with a higher yield and with substantially reduced technological costs than the processes previously known.

What is claimed is:

1. Process for preparing O-(3-amino-2-hydroxy-propyl)-hydroximic acid halides of the formula I wherein R$^1$ is phenyl, or pyridyl or thienyl or substituted phenyl, wherein the one or more substituent(s) may be halo and/or haloalkyl and/or nitro, X is halo, R$^2$ and R$^3$ are independently from each other straight or branched lower alkyl or R$^2$ and R$^3$ together with the nitrogen connecting thereto form a 5 to 7-membered saturated heterocyclic group which may contain additional hetero atom and may be substituted, and the acid addition salts and optically active forms thereof by reacting a carboxamide oxime of the formula (II) wherein R$^1$ is as specified above with reactive 3-amino-2-hydroxy-propane derivative, diazotizing the O-substituted carboxamide oxime thus obtained with sodium nitrite in the presence of hydrogen halide, decomposing the diazonium salt and if desired, separating the optically acive enantiomers and/or reacting the resulting base with an organic or mineral acid, characterized in that the carboxamide oxime of the formula (II) is reacted with a 3-hydroxy azetidinium salt of the formula (III) wherein R$^2$ and R$^3$ are as defined above and Y$^-$ is a salt forming anion in a C$_{1-4}$ alcoholic, medium optionally containing water and made alkaline with an alkali hydroxide, and before diazotizing the O-substituted carboxamide oxime intermediate obtained, the reaction mixture is neutralized and the organic solvent is removed.

2. The process of claim 1 characterized by using ethanol as C$_{1-4}$ alcohol.

* * * * *